(12) United States Patent
Harris et al.

(10) Patent No.: US 6,181,411 B1
(45) Date of Patent: Jan. 30, 2001

(54) APPARATUS FOR INSPECTING DIFFICULT TO ACCESS OBJECTS

(75) Inventors: William Harris; Gregory Yadzinski, both of Farmington; David Prelewitz, Henrietta, all of NY (US)

(73) Assignee: R. Brooks Associates, Inc., Ontario, NY (US)

( * ) Notice: Under 35 U.S.C. 154(b), the term of this patent shall be extended for 0 days.

(21) Appl. No.: 09/134,862

(22) Filed: Aug. 14, 1998

Related U.S. Application Data

(60) Provisional application No. 60/055,624, filed on Aug. 14, 1997.

(51) Int. Cl.[7] .............................. G01C 3/08; G01N 21/00

(52) U.S. Cl. ........................................ 356/4.01; 378/241

(58) Field of Search .................. 356/4.01, 141.5, 356/378, 241; 348/197

(56) References Cited

U.S. PATENT DOCUMENTS

| 4,199,258 | * | 4/1980 | Dav ..................................... 356/378 |
| 4,340,302 | * | 7/1982 | Oku ..................................... 356/241 |
| 5,235,398 | * | 8/1993 | Miller et al. ............................ 356/5 |
| 5,784,098 | * | 7/1998 | Shoji et al. ............................ 348/45 |
| 5,895,927 | * | 3/1999 | Brown ............................. 250/559.19 |

* cited by examiner

Primary Examiner—Mark Hellner
(74) Attorney, Agent, or Firm—Harter, Secrest & Emery LLP; Stephen B. Salai, Esq.; Brian B. Shaw, Esq.

(57) ABSTRACT

Apparatus for inspecting the surfaces of inaccessible objects such as the components of a nuclear power plant steam generator includes: an articulated inspection wand having a proximal end and a distal end movable into position adjacent the surface to be inspected, a laser light source located remotely from the distal end, first and second position sensing detectors located remotely from the distal end of the wand, first and second extending imaging light guides extending from the laser light source, and the position sensing detectors to the distal end of the wand.

13 Claims, 4 Drawing Sheets

Detail of Probe Section

APPARATUS FOR INSPECTING DIFFICULT TO ACCESS OBJECTS

This application claims priority from Provisional Application 60/055,624 filed Aug. 14, 1997.

BACKGROUND OF THE INVENTION

This invention relates to apparatus for inspecting objects in difficult to access locations, and more particularly to apparatus for inspecting and making measurements of the surfaces of components of nuclear power plant steam generators.

There is a need for tools specifically designed for inspecting the internal components of nuclear power plant steam-generators and associated components. The steam-generator functions as a heat exchanger; transferring energy between (primary) water circulating through the reactor core to (secondary) water circulating through the generator turbine. Though the water on the secondary side is maintained at a high level of purity, high temperatures, trace chemicals, and rapid fluid flow rates lead to scouring and corrosion of the steam-generators internal parts and associated plumbing. Chemical action and re-deposition leads to a problem of on-going accumulating deposits on critical surfaces on the secondary side such as flow tubes and support plate surfaces. This type of deposit accumulation can lead to a serious reduction in heat transfer efficiency, flow-tube cracking, and mechanical loading of internal parts.

To effectively monitor the progression and effects of corrosion and accumulating deposits it is necessary to perform visual inspections on the secondary side of the steam-generators interior parts and associated plumbing. The devices shown in U.S. Pat. Nos. 5,544,206, 5,265,129 and co-pending application Ser. No. 08/874,139 can perform this type of inspection effectively. As a result of the systems capabilities of these devices, regular internal visual inspections of nuclear power-plant steam-generators have become an important and necessary part for many plant maintenance programs. Despite the success of the current devices, there is a need to improve and expand inspection capabilities. Currently, the data provided by known inspection systems is in the form of simple 2-Dimensional (2-D) video imagery. Visual data is typically collected by a miniature CCD (Charge-Coupled-Device) camera mounted on the end of a telescoping boom or extendible wand/telescoping boom combination. The extendible boom moves the camera and associated hardware through narrow slots within the steam-generators support plates to a point of interest. The acquired video inspection data from the mounted camera is then stored on video tape for post analysis and evaluation. Lacking depth information, there is no way to accurately measure distances from the observed video images. Hence, valuable corrosion and deposit thickness information cannot be analytically determined. This type of information would be valuable to nuclear plant managers because it would give them the ability to track the rate of steam generation degradation given subsequent and similar inspections. It is an object of this invention to provide a 3-Dimensional (3-D) profiling system to accurately determine spatial information from an inspected image field.

It is another object of this invention to provide apparatus of the type heretofore known having an articulated inspection wand having a three-dimensional profiling system integrated therewith that is small enough to be moved into position to inspect components of a nuclear power plant steam generator. Briefly stated, and in accordance with a presently preferred embodiment of the invention, apparatus for inspecting the surfaces of inaccessible objects such as the components of a nuclear power plant steam generator includes: an articulated inspection wand having a proximal end and a distal end movable into position adjacent the surface to be inspected, a laser light source located remotely from the distal end, first and second position sensing detectors located remotely from the distal end of the wand, first and second extending imaging light guides extending from the laser light source, and the position sensing detectors to the distal end of the wand.

In accordance with another aspect of the invention, first and second optical lenses are disposed at the distal ends of the second and third imaging light guides for forming an image of the surface to be inspected.

In accordance with another aspect of the invention, focusing lenses are positioned between the proximal ends of the extended imaging light guides and the first and second position sensing detectors.

In accordance with another aspect of the invention, a two-dimensional scanner is disposed between the laser light source and the proximal end of the first extended imaging light guide.

In accordance with another aspect of the invention, an image capturing device, such as a video camera is optically coupled to the second extended imaging light guide.

In accordance with a still further aspect of the invention, an illumination light source is coupled to at least one of the second and third extending imaging light guides, for providing illumination of the surface for the video camera.

In accordance with another aspect of the invention, beam splitters are provided at the proximal ends of the imaging light guides for coupling the light guides to the illumination sources and the position sensitive detectors.

BRIEF DESCRIPTION OF THE DRAWINGS

The novel aspects of the invention are set forth with particularity in the appended claims. The invention itself, together with further objects and advantages thereof may be more readily comprehended by reference to the following detailed description of a presently preferred embodiment of the invention taken in conjunction with the accompanying drawing, in which:

DETAILED DESCRIPTION OF THE PREFERRED EMBODIMENT

Figure 1:
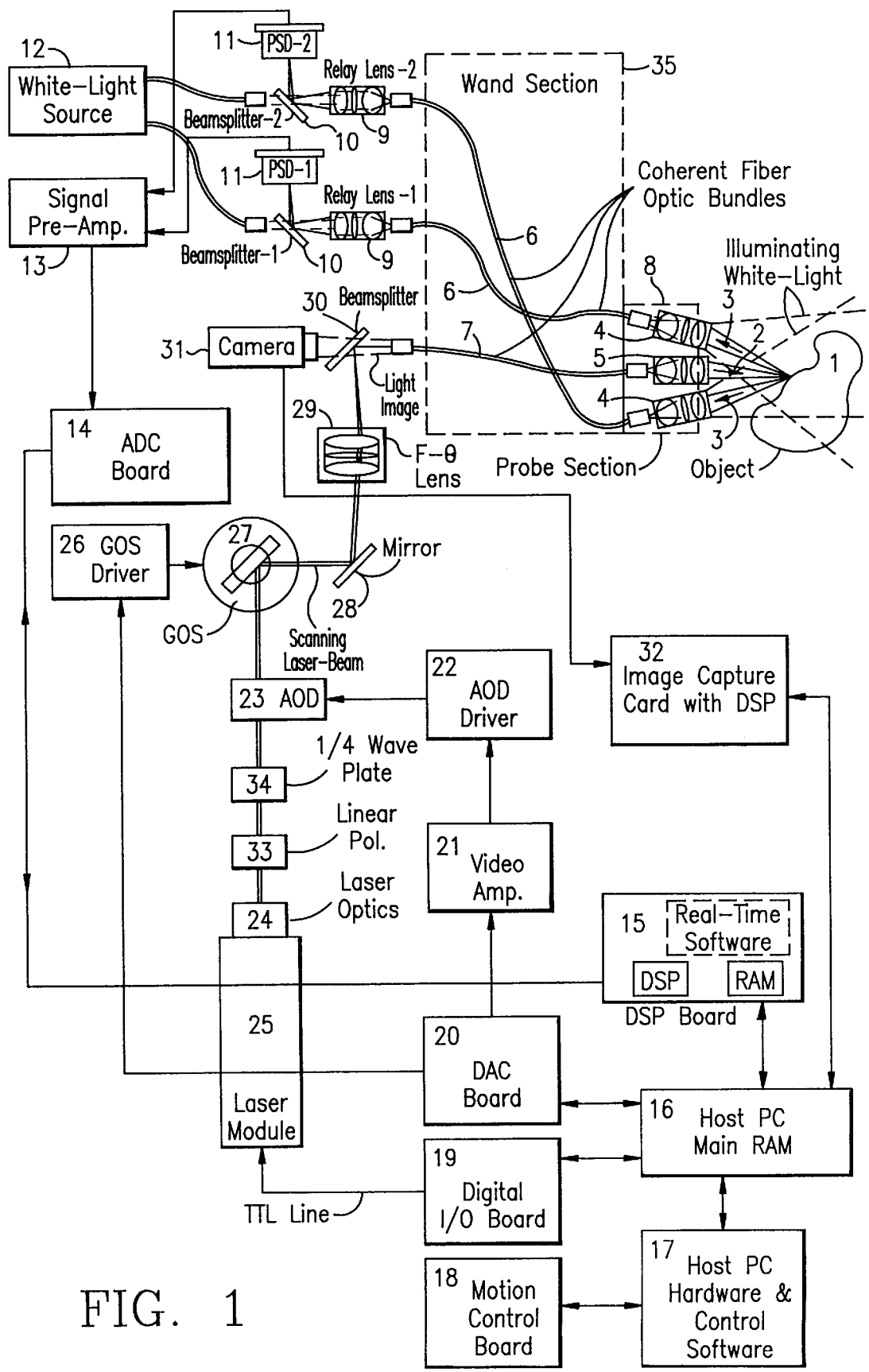
FIG. 1 is an overall system diagram of the apparatus for inspecting difficult to access objects in accordance with this invention.

FIG. 1 illustrates the basic components of the apparatus of this invention, hereinafter referred to as IVIS. The basic theory of operation for the 3-D profiling system is to perform a 2-D scan throughout an object volume space 1 (the inspection space) with a narrow laser beam 2 and measure the light scattered 3 using a pair of large area Position-Sensing-Detectors 11 (PSD). Using the PSD data for triangulation, the 3-D position of the scattered laser spot 3 can be determined with respect to the detector probe 8 position. Hence, by scanning the whole object space 1 within the optical field of view and storing the measured dimensional data, a total 3-D object space profile can be created. Given prior knowledge about the steam-generators internal component layout, geometry, and dimensions (with no corrosion or deposit accumulation), comparisons can be made with the actual 3-D inspection data taken by the IVIS. By comparing the data, spatial deviations are determined between actual and pristine component dimensions. Therefore, the thickness of the observed accumulated deposits as well as other surface dimensional information can be analytically determined.

Steam-generator inspection systems are subject to the space restrictions and unique geometry's encountered in the steam-generator environment. Component sizes need to remain small so that the probe head can be maneuvered effortlessly through the structure. Existing robotic systems such as R. Brooks Associates Upper-Bundle-In-Bundle (UBIB) steam-generator inspection device can be utilized with the present invention. This robot incorporates many mechanical servo systems that properly position a compact video-probe inside the steam-generator. Space is extremely limited. The entire robot assembly must be inserted through an access port that is approximately 6 inches in diameter. Once inside, the robot has a extendible main-boom that can lengthened to approximately 30 feet in height. The boom and elevated apparatus cannot be any wider than the steam-generator support plate slots, which are approximately 2 inches wide. On top of the extendible boom is the video probe assembly that consists of an extendible wand, video cameras, and lighting system. The wand can rotate in a large arc about a shoulder connection at the end of the boom. A miniature CCD camera, fixed focus lens, and two small light sources make up the video-probe on the inspection end of the wand. The probe is very compact and narrow so that it can fit between the steam-generator tube bundles. The current wand/probe combination allows steam-generator tube separations of approximately 8 mm or greater to be inspected.

The additional equipment requirements for the IVIS as compared to the standard UBIB inspection system require a complete redesign of the probe layout. Probe size and weight restrictions stipulate this. FIG. 1 illustrates these changes. In accordance with this invention, extending imaging light guides, preferably, coherent fiber optical bundles or systems including mirrors, are used extensively to transport both light and images. As a result, all electrical circuits in the wand and probe especially those at the distal end are eliminated. The other system design change is the inclusion of the 3-D laser scanning and measuring components.

To get a better idea of the system dynamics, we'll step through small increments in time and describe what each of the components illustrated in FIG. 1 is doing. Starting with the control and processing software on a host PC (personnel computer), a user defines the parameters for the IVIS. Input parameters include: locating the 3-D probe position relative to the steam-generator coordinates, area size and location (relative to the total observed field) over which the laser will spatially scan, the density of 3-D data samples to be acquired over the defined scan volume, and the volume scan refresh rate (i.e. how often is the volume re-scanned in time). The Digital-Signal-Processor 15 (DSP) hardware controls the timing of all the other IVIS hardware components. The PC host control software 17 downloads a set of executable instructions, including user parameters, to the DSP 15. The status and availability of each PC hardware component is confirmed before the DSP executes the scanning instructions. When all systems are ready, the DSP 15 sends a command to the DAC board 20 via the PC's PCI bus to output a specific voltage. The voltage signal determines the optical deflection state of the acousto-optical-deflector (AOD) 23. However, the voltage from the DAC is of insufficient voltage or current output to be an effective signal for the AOD driver 22 so the signal is conditioned with a video amplifier circuit 21. The AOD driver 22 in our case needs a voltage swing of +4 to +17 Volts, which the video amplifier 21 provides. The output of the AOD driver 22 is in the form of an RF (radio frequency) signal which is then applied to the AOD 23 crystal. The applied RF signal sets up a traveling sound wave with a frequency directly proportional to the input RF frequency, which is in a range of 60 and 100 MHz. The AOD 23 controls the horizontal laser scan dimension and was chosen due to its compact size and fast response time, which is on the order of 12 microseconds per scan position. In conjunction with the AOD, the DSP also instructs the DAC to send an additional voltage output (−10 to+10 Volts) to the galvanometric optical scanner (GOS) driver 26 circuit. As the name implies, the GOS driver controls the mirror scan position on the GOS 27. The GOS's mirror is magnetically deflected by a certain angle, which is determined by the applied voltage from the DAC 20. The GOS 27 controls the vertical laser scan dimension.

Once the horizontal and vertical scanning positions have been set, the system is now ready to launch a laser pulse into the object space. At this time, the DSP 15 board sends a timing pulse to the digital I/O board 19, which then passes a TTL pulse on to the laser and associated driver circuits 25 within the laser module. This activates the emission state of the laser. The laser is a single-mode, 656 nm semiconductor diode laser with a maximum CW (continuous wave) output of 40 mW. At the output of the laser there are special optics 24 that circularize and collimate the laser beam output. The collimated beam has a diameter of approximately 3 mm. The additional optics drops the laser power output by approximately 50%. In addition to the individual semiconductor laser module, the laser housing module 25 also incorporates a thermal-electric (TE) cooler and current modulation circuits. The TE cooler insures that the case temperature of the semiconductor laser module remains constant. Without the TE cooler the laser output wavelength would drift, which would be detrimental to the overall system performance. This is particularly true for the acousto-optical-deflector device (AOD) 23, which deflects the laser beam via diffraction and is therefore sensitive to wavelength shifts. The laser current modulator circuit allows the laser to be turned on and off with 100% modulation at certain times of the data acquisition process. Laser modulation is at half the data acquisition rate and twice the rate of the laser scan positioning system. For each laser position in object space, the laser output is modulated through two full on-off cycles. The ADC 14 samples at each of the on or off states. The sampled off state signals are averaged and subtracted from the averaged on state signals. Averaging helps reduce sampled signal noise and subtracting out the off state signals removes any background influences. Before entering the AOD 23, the collimated laser light passes through a linear polarizer 33 and zero-order ¼ waveplate 34 combination. This arrangement serves two purposes. First, for maximum efficiency, the AOD 23 requires right-hand-circularly polarized light and the ¼ waveplate 34 provides this. Second, the combination reduces the detrimental effects of back reflections on the semiconductor lasers performance given that the laser energy becomes left-hand circularly polarized upon reflection. At the ¼ waveplate 34, the reflected energy is linearly polarized, but with a 90 degree rotation with respect to the output beam. Hence, reflected laser light is effectively blocked by the linear polarizer 33.

Going forward again after the ¼ waveplate 34, the collimated laser light passes through the AOD 23, which diffracts the laser by a predetermined angular amount in the horizontal direction, and to the GOS 27, which reflects the laser by a predetermined angular amount in the vertical direction. Referring to FIG. 1, the laser light is then reflected by a positioning mirror 28 into a F-theta lens 29, which focuses the scanned laser light onto the face of a coherent fiber optic bundle 7. The F-theta lens 29 has special properties for scanning applications, such as maintaining a flat-field and perpendicular focus spot at the image plane. It also uniformly displaces the focus spot at the image plane with deflection angle changes of the input laser.

As indicated in FIG. 1, before the laser light enters the fiber optic bundle 7, it is reflected by a polarization independent harmonic beam-splitter 30 that is tuned to reflect nearly all the 656 nm laser light into the fiber optic bundle 7. On the backside of the beam-splitter 30 a CCD camera 31 is used to monitor the rest of the visible spectrum that is back reflected from the object plane 1 through the fiber bundle 7.

Figure 3:
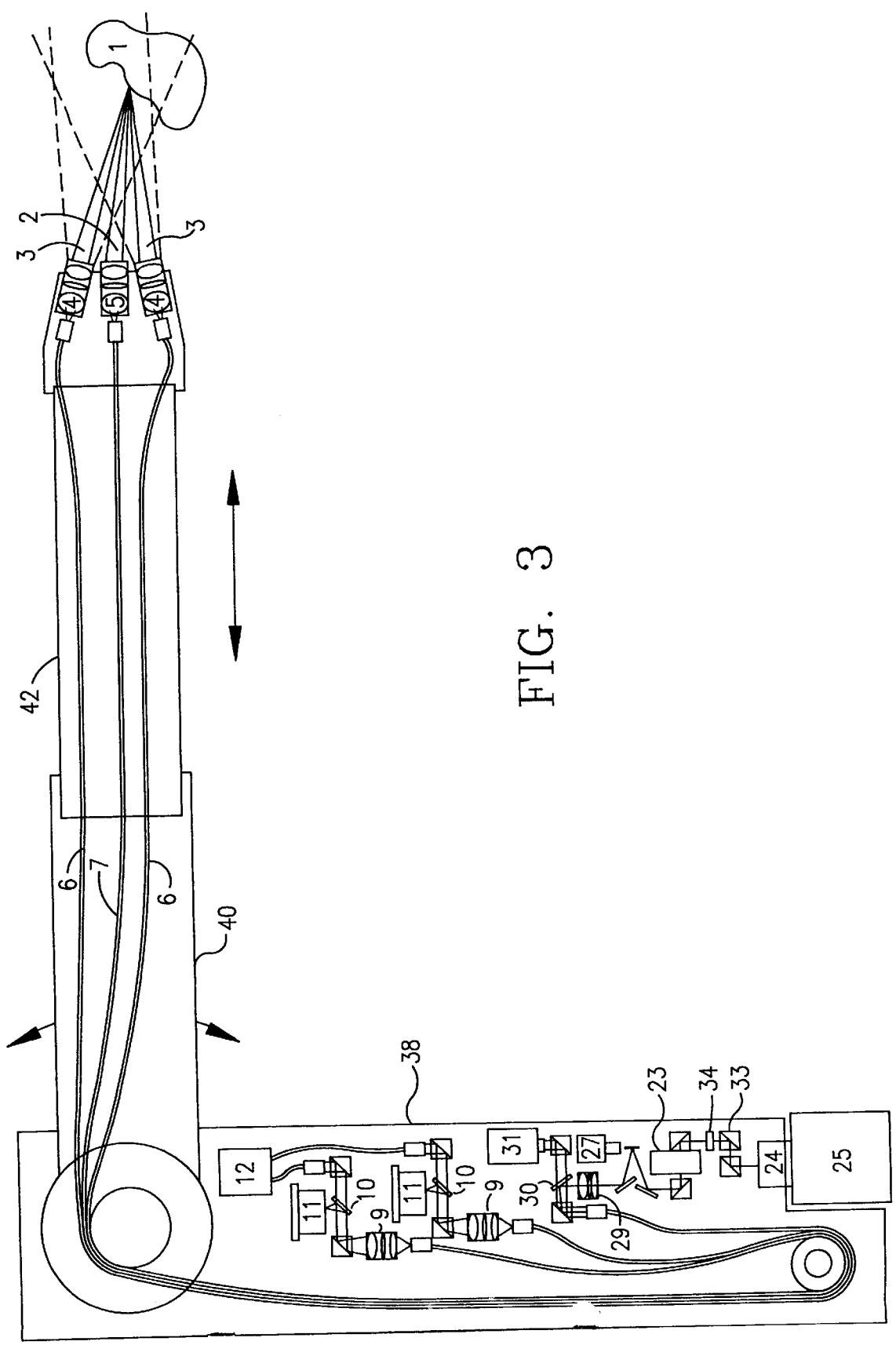
FIG. 3 is a diagrammatic illustration of an inspection device incorporating the invention.

Inspection apparatus incorporating the 3-D profiling functions of this invention is illustrated at FIG. 3. A housing 38 which contains all of the components of the invention heretofore described in connection with FIG. 1 is attached to the upper end of an extendible boom, not shown, which itself is attached to a horizontally extending second boom, also not shown. This construction is generally known, for example, from prior U.S. Pat. Nos. 5,265,129, 5,544,206 and co-pending application Ser. No. 08/874,139, the contents of which are incorporated by reference.

At the upper end of housing 38, a wand 40 is pivotally attached for movement into the inaccessible location. Preferably, wand 40 includes an extendible portion 42, to which the probe head is attached.

Figure 2:
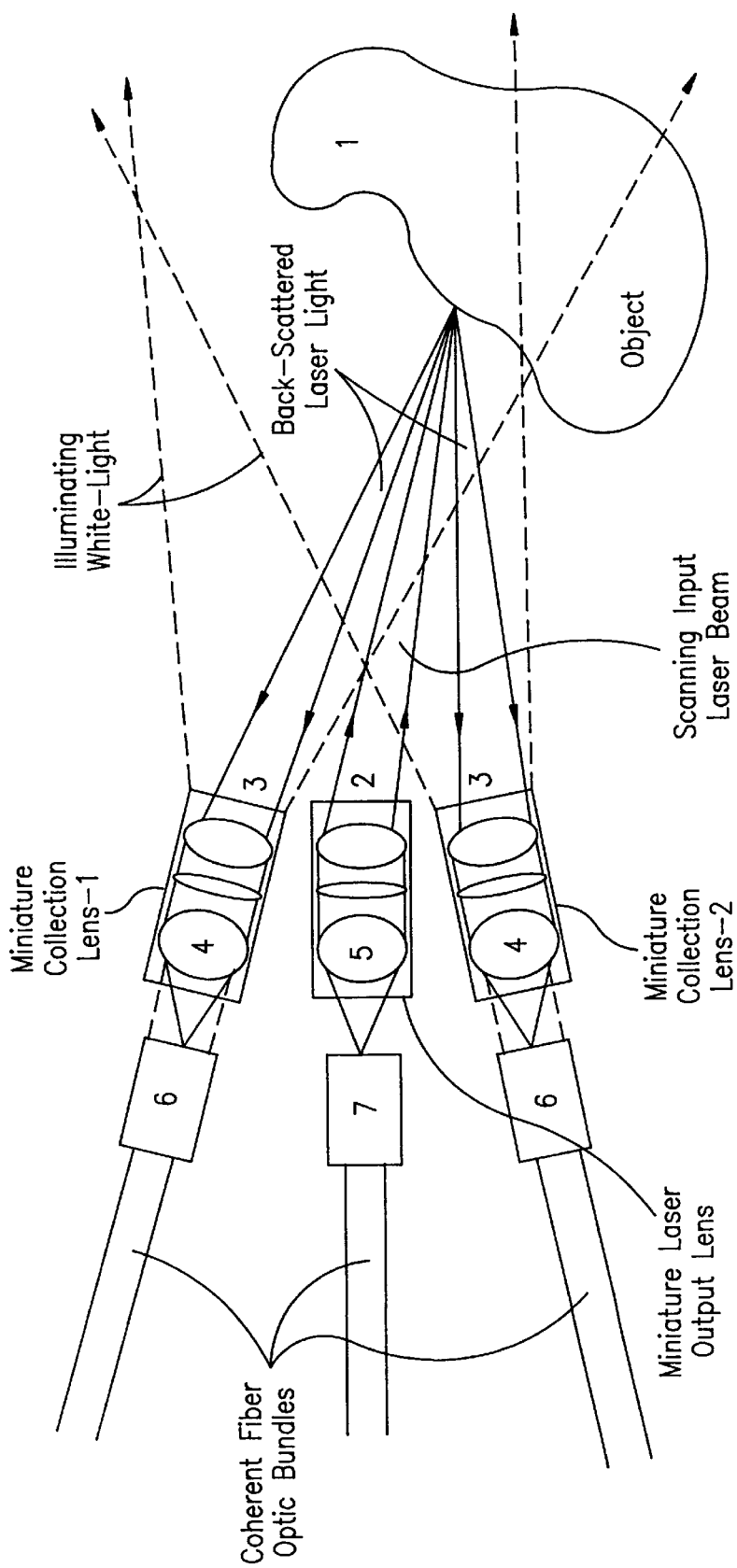
FIG. 2 is an enlarged view of the portion of the apparatus of FIG. 1 that is moved into position adjacent the object to be inspected.

As illustrated, the laser light travels through the fiber bundle 7, which is encased by a wand assembly 35 (FIG. 3) and is output through a miniature imaging lens 5 at the probe-head 8 (FIG. 2). The laser light 2 from lens 5 is then focused into the object space 1 where the laser light is scattered off various surfaces of interest. Lens 5 is specially designed to have a large depth of focus, a flat field, and a long working distance.

The light scattered from the object space 1 is collected by a pair of miniature lenses 4 on either side of the laser scanning lens 5. The collected light is focused onto another pair of coherent fiber optic bundles 6 that transfers the light back through the wand assembly 35 (FIG. 3) to a pair of 2-D PSD's 11. Given the separation distance and angular displacement between the center points of the distal probe end faces of the fiber bundles 6 (FIG. 2), position determination can be calculated mathematically using simple triangulation. Before the light reaches the PSD sensors, the collected laser light passes through a relay lens 9 and is then reflected by another polarization independent harmonic beam-splitter 10 that is tuned to reflect nearly all of the collected 656 nm laser light. This arrangement allows an illumination system 12 to be placed on the backside of the beam-splitter 10, which then supplies visible white lighting (minus the 656 nm line) to the object space via the fiber optic bundles 6. White light (minus the 656 nm laser line) is then back reflected from the object plane 1 through fiber bundle 7. Hence, the coherent fiber optic bundles perform dual roles. Reiterating, two fiber optical bundles 6 collect scattered laser light for the PSD's 11 while also providing general illumination to the object space 1. The center fiber bundle 7 on the probe-head 8 transfers scanned laser 2 light to the object space 1 while also collecting visible light and images for the CCD camera 31 assembly.

The laser light incident on one PSD 11 generates 4 position dependent currents. The currents are converted to voltages and pre-amplified 13 before being sampled by the ADC board 14. The ADC 14 converts the analog voltages to digital representations and sends the results to the DSP 15 for processing. Given the probe head configuration geometry (separation and angle between the center points of the fiber 6 probe-end faces) illustrated in FIG. 2, and the user input parameters, the DSP calculates the position of each sampled laser spot 2 to create a 3-D profile map of the scanned volume. This information is then stored in the host PC's main memory 16.

Once in the computer's memory, the host processing software can manipulate the data in ways that best suits the users needs, such as extracting scale thickness information from flow-tubes. Also, given the object space 1 images captured with the CCD camera 31 and PC capture board 32 system, a real-time overlay of the calculated 3-D data and visual data can be performed.

Figure 4:
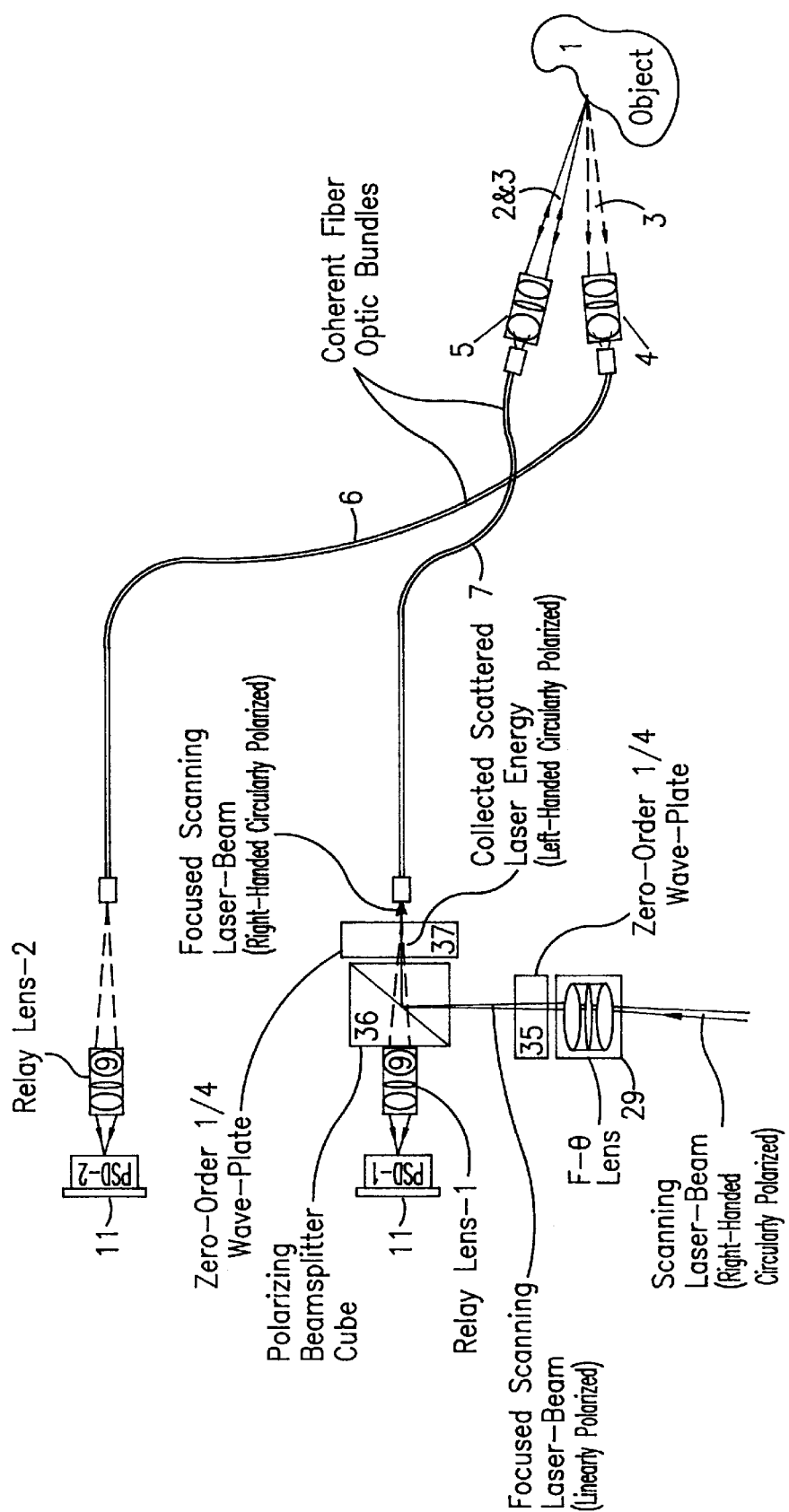
FIG. 4 is a diagrammatic illustration of an embodiment of the invention that includes the 3-D mapping functions, but not the video camera included in the embodiment of FIG. 1.

A variation of this device is considered in FIG. 4. Here, a device using only two coherent fiber optic bundles is employed for scanning the laser beam and capturing the scattered light from the object space 1. In this case, the polarization properties of the laser are utilized to accomplish this. Recalling the system in FIG. 1, the laser light is right-hand-circularly polarized by a combination linear polarizer 33 and zero-order ¼ waveplate 34. After the laser is 2-Dimensionally scanned by the AOD 23 and GOS 27 devices, the beam is focused by a F-θ lens 29. It's at this point that FIG. 4 begins. After passing through the F-θ lens 29, another zero-order ¼ waveplate 36 is employed to linearly polarize the scanning beam so that its orientation is parallel to that of the polarizing beam-splitter 36 for maximum reflection. After reflecting off the beam-splitter cube 37, the scanned laser light passes through another zero-order ¼ waveplate 38, and then through a coherent fiber optic bundle 7. As the light exits the last ¼ waveplate 37, the light is again circularly polarized before entering the fiber bundle 7. At the object 1, the scanned laser light is focused by a miniature imaging lens 5. Light that is back-scattered 3 from the object space 1 is collected by the same lens 5 that provides focusing for the output scanning beam 2. To acquire sufficient data for calculating a 3-Dimensional surface measurement, another miniature lens 4 is used to collect scattered laser energy 2 form another perspective, which is then passed through a second coherent fiber optic bundle 6. Collected light exiting the second fiber bundle 6 then goes through a relay-lens 9 onto a PSD 11 where the signal data is collected and processed the same as was described for the device in FIG. 1.

The collected laser light exiting the first fiber bundle 7 is processed slightly differently. Recall that the scanned laser light 2 is circularly polarized before transmission to the object space 1. Once the light is scattered, the reflected laser energy 3 will retain much of its circular polarization nature but with its polarization vector rotating opposite to the incident light 2. Hence, as the collected scattered light 3 passes through the ¼ waveplate 37, the polarization will be made linear again but with a perpendicular orientation to that of the polarizing beam-splitter 36. As a result, most of the returning light energy will pass through the beam-splitter cube 36 to the relay lens 9 and then to the PSD 11. Again, the data is collected and processes at this point just the same as was described for the device in FIG. 1.

While the invention has been described in connection with a presently preferred embodiment thereof, those skilled in the art will recognize that many modifications and changes may be made therein without departing from the true spirit and scope of the invention, which accordingly is intended to be defined solely by the appended claims.

What is claimed is:

1. Apparatus for inspecting the surfaces of inaccessible objects comprising:
    an articulated inspection wand having a proximal end and a distal end movable into position adjacent a surface to be inspected;
    a laser light source located at the proximal end of the inspection wand;
    first and second position sensing detectors located at the proximal end of the wand;
    a first extended imaging light guide extending from the laser light source to the distal end of the wand;
    a second extended imaging light guide extending from the first position sensing detector to the distal end of the wand;
    a third extended imaging light guide extending from the second position sensing detector to the distal end of the wand.

2. The apparatus for inspecting the surfaces of inaccessible objects of claim 1 comprising:
    a first optical lens located at the end of the first extended imaging light guide disposed at the distal end of the wand; and
    second and third optical lenses located at the ends of the second and third extended imaging light guides disposed at the distal end of the wand.

3. The apparatus for inspecting the surfaces of inaccessible objects of claim 1 comprising:
    fourth and fifth lenses disposed between a proximal end of each of the second and third extended imaging light guides and the first and second position sensing detectors.

4. The apparatus for inspecting the surfaces of inaccessible devices of claim 1 comprising a 2-Dimensional scanner disposed between the laser light source and the proximal end of the first extended imaging light guide.

5. The apparatus for inspecting the surfaces of inaccessible objects of claim 1 comprising an image capturing device coupled to the first extended imaging light guide.

6. The apparatus for inspecting the surfaces of inaccessible objects of claim 5 comprising a first beam splitter disposed between the image capturing device, the laser light source, and the proximal end of the first extended imaging light guide.

7. The apparatus for inspecting the surfaces of inaccessible objects of claim 6 comprising second and third beam splitters and first and second illuminating light sources disposed adjacent the proximal ends of the second and third extended imaging light guides respectively.

8. The apparatus for inspecting the surfaces of inaccessible objects of claim 1 comprising an image processing device or circuit connected to the first and second 2-Dimensional position sensing detectors.

9. The apparatus for inspecting the surfaces of inaccessible objects of claim 7 comprising fourth and fifth lenses disposed between the first and second illumination light sources and the second and third optical beam splitters respectively.

10. A method of making surface contour measurements in inaccessible areas comprising:
    providing an inspection wand movable into proximity with the inaccessible areas;
    providing a laser illumination source remote from the inaccessible area;
    providing a 3-Dimensional surface detector remote from the inaccessible area;
    coupling a proximal end of a first extended imaging light guide to the laser illumination source;
    coupling a proximal end of a second extended imaging light guide to the 3-Dimensional surface detector;
    positioning a distal end of each of the first and second extended imaging light guides at the distal end of the inspection wand;
    scanning the laser illumination source across the surface to be measured; and
    detecting light scattered from the surface to be measured with the 3-Dimensional surface detector.

11. The method of making surface contour measurements in inaccessible areas of claim 10 comprising:
    providing an image capturing device remote from the inaccessible area;
    coupling the image capturing device to a proximal end of a third extended imaging light guide;
    positioning a distal end of the third extended imaging light guide adjacent the distal end of the inspection wand.

12. The method for making surface contour measurements in inaccessible areas of claim 11 comprising:
    coupling an illumination light source to the proximal end of one of the first and second extended imaging light guides.

13. Apparatus for inspecting the surfaces of inaccessible objects comprising:
    an articulated inspection wand having a proximal end and a distal end movable into position adjacent a surface to be inspected;
    a laser light source located remotely from the distal end of the inspection wand;
    first and second position sensing detectors located remotely from the distal end of the wand;
    a first extended imaging light guide extending from the laser light source to the distal end of the wand;
    a second extended imaging light guide extending from the first position sensing detector to the distal end of the wand;
    a third extended imaging light guide extending from the second position sensing detector to the distal end of the wand.

* * * * *